United States Patent
Galbiati

(10) Patent No.: US 12,305,160 B2
(45) Date of Patent: May 20, 2025

(54) PHOTOBIOREACTOR FOR BLUE-GREEN ALGAE CULTIVATION

(71) Applicant: Cristiano Galbiati, Carloforte (IT)

(72) Inventor: Cristiano Galbiati, Carloforte (IT)

(73) Assignee: Fondazione Aria—Ente del Terzo Settore, Cagliari (IT)

( * ) Notice: Subject to any disclaimer, the term of this patent is extended or adjusted under 35 U.S.C. 154(b) by 962 days.

(21) Appl. No.: 17/424,517

(22) PCT Filed: Jan. 30, 2020

(86) PCT No.: PCT/IB2020/050751
§ 371 (c)(1),
(2) Date: Jul. 21, 2021

(87) PCT Pub. No.: WO2020/157698
PCT Pub. Date: Aug. 6, 2020

(65) Prior Publication Data
US 2022/0135932 A1 May 5, 2022

(30) Foreign Application Priority Data
Jan. 31, 2019 (IT) .......................... 102019000001449

(51) Int. Cl.
| C12M 1/00 | (2006.01) |
| C12M 1/12 | (2006.01) |
| C12M 1/34 | (2006.01) |
| A23L 29/269 | (2016.01) |

(52) U.S. Cl.
CPC ............ *C12M 47/10* (2013.01); *C12M 21/02* (2013.01); *C12M 23/06* (2013.01); *C12M 23/22* (2013.01); *C12M 29/12* (2013.01); *C12M 29/18* (2013.01); *C12M 29/20* (2013.01); *C12M 29/24* (2013.01); *C12M 41/40* (2013.01); *C12M 47/02* (2013.01); *A23L 29/269* (2016.08)

(58) Field of Classification Search
CPC ...... C12M 47/10; C12M 21/02; C12M 23/06; C12M 23/22; C12M 29/12; C12M 29/18; C12M 29/20; C12M 29/24; C12M 41/40; C12M 47/02; C12M 29/14; A23L 29/269
See application file for complete search history.

(56) References Cited

U.S. PATENT DOCUMENTS

| 2010/0068801 A1* | 3/2010 | Woods | .................. C12M 27/20 |
| | | | 435/292.1 |
| 2015/0315534 A1* | 11/2015 | Vargas, Jr. | ............. C12M 29/04 |
| | | | 435/292.1 |

FOREIGN PATENT DOCUMENTS

| CN | 1760358 A | * | 4/2006 | ............ C12M 21/02 |
| FR | 2685344 A1 | * | 6/1993 | ................ C02F 3/32 |
| WO | 2010002745 A1 | | 1/2010 | |

* cited by examiner

*Primary Examiner* — John McGuirk
(74) *Attorney, Agent, or Firm* — Jose Cherson Weissbrot

(57) ABSTRACT

The present invention concerns the field of high-efficiency, quality-controlled production of blue-green algae for direct human consumption, for extraction of proteins, vitamins, and amino acids, and for production of organic materials loaded with the special isotope 13C.

It is an object of the present invention to describe a high-efficiency photobioreactor.

9 Claims, 1 Drawing Sheet

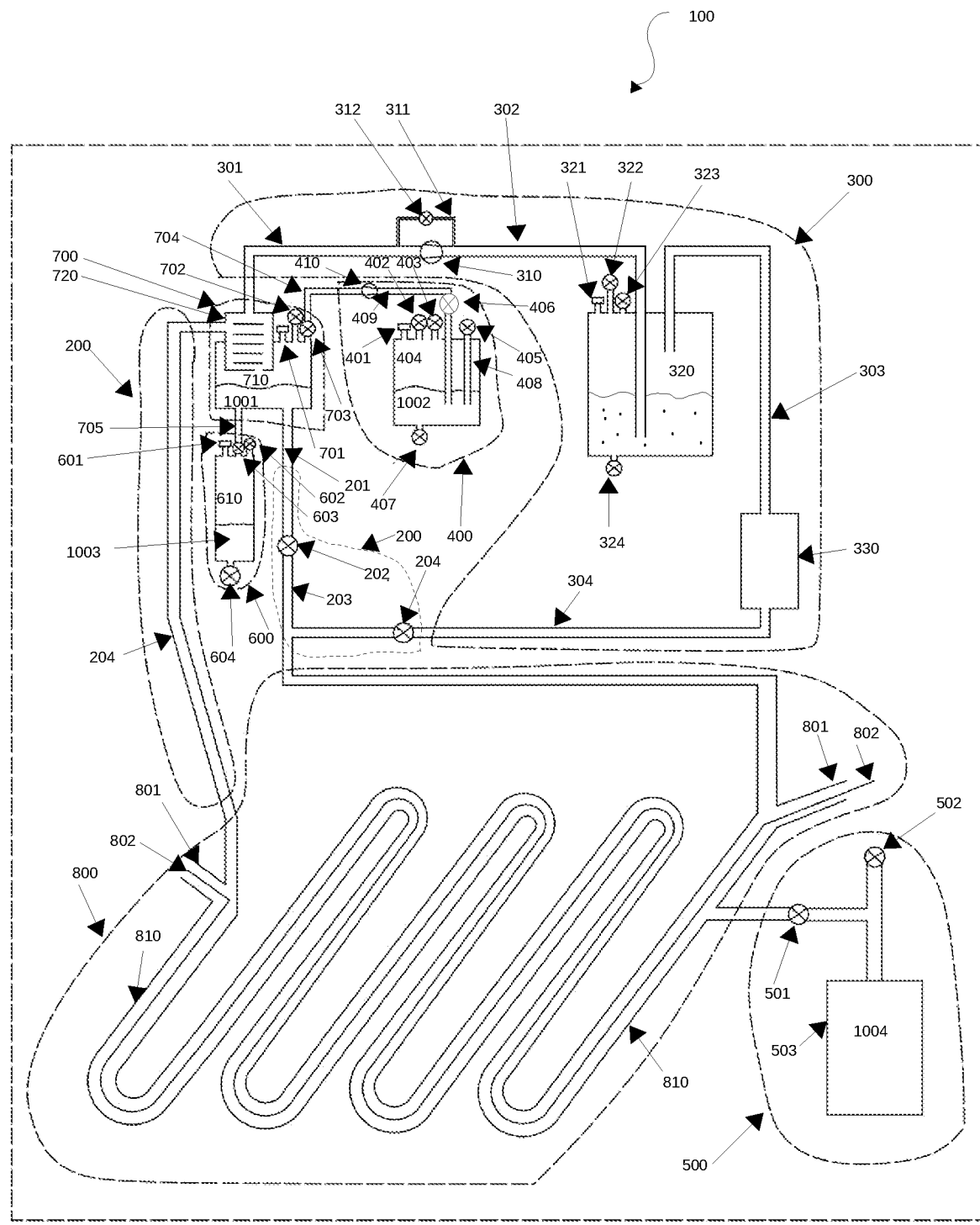

PHOTOBIOREACTOR FOR BLUE-GREEN ALGAE CULTIVATION

TECHNICAL FIELD

The present invention concerns the field of high-efficiency, quality-controlled production of blue-green algae for direct human consumption, for extraction of proteins, vitamins, and amino acids, and for production of organic materials loaded with the special isotope $^{13}C$.

PRIOR ART

It is known by the person skilled in the art that blue-green algae, a form of bacteria known as cyanobacteria, were responsible for the early oxygenation of the Earth atmosphere: they reproduce consuming carbon dioxide ($CO_2$) and producing oxygen ($O_2$), and they are therefore photosynthetic and autotrophic. Blue-green algae are naturally found in fresh water lakes and in tropical or subtropical waters. Some naturally occurring blue-green algae are used for human consumption in regions of Mexico and Africa. When grown under controlled conditions, such as to make sure that any contamination from toxin-generating bacteria and heavy metals are absent, blue-green algae can be used as an excellent source of dietary proteins, vitamins, amino acids, and minerals. Today, they are used in weight loss program, as a supplement in vegetarian or vegan diets, as well as to fight a number of ailments, such as attention deficit-hyperactivity disorder, diabetes, stress, fatigue, anxiety, depression, hayfever, and premenstrual syndrome. Two particular cyanobacteria, Asthrospira Platensis and Arthrospira Maxima, also known under the name of Spirulina, are particularly useful for human consumption. Spirulina reproduces by binary fissions, and has small gas vesicles that make it buoyant in its aquatic environment. Spirulina is very high in its nutrients contents (vitamins, proteins, essential amino acids, minerals, no fats), representing an ideal supplement for the diet of astronauts; it contains a large quantity of C-phycocyanin, a pigment-protein complex from the light-harvesting Phycobiliprotein family, which is a powerful anti-oxidant and anti-inflammatory, known to reduce the risk of cancer, as well as to exercise functions of protection of the brain and the liver, especially by reducing oxidative stress induced by Reactive Oxygen Species (ROS); spirulina also lowers bad LDL, raises good HDL, controls glycemia leading to diabetes, well documented anti-hyperlipemic and anti-hypertensive effects; it protects bad LDL from oxidation, a key driver of many diseases, including cardiovascular, neurological, and non-alcoholic fatty liver diseases and diabetes; it is known to reduces occurrence of cancer in lab tests on animals and reverses oral leukoplakia in humans; it reduces blood pressure; it fights anemia, fatigue, and improved immune function; improves muscle strength and endurance; it lowers blood sugar levels; last, but not least, spirulina lowers the risk of diabetes complications [Shih: 2009gb, Farooq:2014hy, Kamarei: 1985gk, Parikh:2001fs, Mazokopakis:2013bu, TorresDuran:2007ba, Park:2008ks, Ismail:2015hf, Ku:2013ck, Lee:2008fy, Ismail:2009up, Akao:2009hp, Mathew: 1995fj, Bhavana:2013hp, Selmi: 2011im, Kalafati:2010ho, Lu:2006je, Ou:2012jw, Ou:2013gf, Jarouliya:2012uy]. Spirulina can also be used as an additive in fertilizers.

Given its ability to readily consume CO2 and produce organic material, the growth of spirulina is a preferred method for the production of organic materials labeled in the rare stable isotope $^{13}C$, starting from feed sources of carbon labeled in $^{13}C$, which typically are available in inorganic form $^{13}CO$ and $^{13}CO_2$. Proteins, vitamins, and amino acids labeled in $^{13}C$ can be directly extracted from $^{13}C$-spirulina and further processed to produce in laboratory thousands of organic molecules labeled in $^{13}C$. $^{13}C$-labeled molecules find a wide range of uses in test procedures in use in the fields of molecular biology, proteomics, and the development of advanced drugs. As an example of a recently introduced procedure, thanks to the strong nuclear magnetic moment of $^{13}C$, $^{13}C$-labeled substances can be HyperPolarized (HP) by aligning their nuclear magnetic moments in a preferred direction by dynamic nuclear polarization and then injected in form of a liquid solution in live organism, where they can be traced through HyperPolarized Magnetic Resonant Imaging (HP-MRI), which provides spatial as well as chemical information, allowing to probe and study specific metabolic and proteomic pathways.

Growth of blue-green algae (and spirulina) requires a cultivation medium, which is obtained by adding $CO_2$ to a culture medium that is a fluid rich in minerals. Controlled growth of blue-green algae requires a closed containment system of the cultivation medium, constant monitoring of the concentration of minerals, $CO_2$, and pH, and quality control of final the products. Controlled growth of $^{13}C$-labeled blue-green algae requires, in addition, complete separation of the cultivation fluid from the atmosphere: all the $CO_2$ fed into the cultivation fluid must be labeled in $^{13}C$; also, preferably, all intake of carbon is limited to the $^{13}CO_2$, thus requiring the suppression of all other intake avenues of carbon must hence the use of a decarbonated cultivation medium and. Excess dissolved oxygen (DO) produced by the photosynthesis process fixing $CO_2$ into organic material is generally toxic for the blue-green algae and its presence in the cultivation stream hinders the production of blue-green algae biomass. Growth of blue-green algae and of spirulina in particular is only possible within a narrow range of temperatures: the ideal range for the growth of spirulina, for example, is limited to 25-35° C.: the culture will die if the temperature raises above 40° C. or drops below 10° C.

The two mains classes of farming of blue-green algae are open systems, where the cultivation fluid is exposed to open air, and closed systems, with the cultivation fluid somewhat separated from the atmosphere, allowing sterility in the culture medium. Open systems can consist of open ponds or raceway systems. In open systems, the production of blue-green algae depends strongly on parameters driven by the environment. Closed systems can be further subdivided in photobioreactors (PBRs), where a high amount of light is responsible to trigger the photosynthesis, of fermenters, which allow for growth of blue-green algae consuming organic carbon (typically, glucose) in the dark. Photobioreactors can be arranged in the form of flat panel reactors, tubular reactors, or bag reactors: in any circumstance the containment system of the cultivation fluid must be made of transparent or translucent materials to permit the efficient transmission of light. The light input can come either from sunshine and ambient light or from artificial sources.

Blue-green algae are delicate organisms and require particular conditions for efficient growth.

The reproduction of these photosynthetic and autotrophic organisms is driven by the photosynthesis triggered by visible light. When photosynthesis is driven by artificial light (as opposed to sunlight), the growth of the blue-green algae is optimized by the provision of a light spectrum matching the specific absorption spectrum of the algae. The photobioreactors must be built from transparent materials to enable transmission of light to the cultivation fluid, and care must be given to optimize light transmissivity and thickness of the construction materials.

The temperature range set for proliferation of blue-green algae is very precisely set and typically narrow. For example, for spirulina it is limited to the range from 20° C. to 35° C.; when temperature is raised above 40° C. or dropped below 5° C. the spirulina quickly dies. It is therefore important to provide in a photobioreactor means of stabilization of the temperature. A photobioreactor designed to sustain a massive production of blue-green algae would benefit of installation in a luminous environment, such as to profit maximally of the sunlight, and in a temperate climate. Installation in a temperate climate would still require the presence of an active thermal stabilization loop if the plant is intended for year-round operation. This mode of operation is particularly valuable in presence of the availability of important thermal sources of degraded heat, able to supply heating up to the temperature of 35° C. but not useful for industrial and/or domestic uses. This is the case of some special thermal sources, including some exhaust water streams extracted from deep mines.

The speed of circulation of the cultivation fluid is another essential parameter. Stationary fluids must be avoided to limit growth on surfaces. The speed of circulation must be relatively high to restraint growth on the surfaces of the containment systems and restrict growth to the cultivation medium. The system driving the circulation of the cultivation fluid must be sufficiently gentle: the direct mechanical action of pumps contacting the blue-green algae, for instance, can break their cells and result in permanent modification of their structure and in alteration of their nutritional content.

In the prior art, photobioreactors were developed as enclosed system to allow for almost complete separation from the atmosphere and hence for sterility. Photobioreactors were combined with heat exchangers to permit heating of the cultivation fluid. They were built of transparent or translucent materials to allow for the effective transmission of light. Photobioreactors also included air-driven mechanisms capable of inducing the high-speed forced recirculation of the fluid, in particular the so called airlift mechanism, well described in Ref. [AcienFernandez:2001en] as "An airlift-driven photobioreactors with a continuous run tubular solar receiver essentially consists of two parts, the airlift system and the looped solar receiver. The airlift device serves to circulate the culture through the solar receiver. A gas-liquid separator in the upper zone of the airlift column prevents gas bubbles from recirculating into the solar loop. As photosynthesis occurs in the solar tubing, oxygen accumulates and it is stripped out in the airlift zone when the fluid returns from the solar loop. The relevant design aspects are discussed next, separately for the two zones."

This particular mechanism is effective in reducing the shear and stress on spirulina but, disadvantageously, does not allow the complete sterility of the cultivation fluid as air is continuously injected in the cultivation medium both to provide the forced recirculation of the fluid (thus providing also a minimal concentration of carbon dioxide). A trivial modification of this system would consist into the injection of nitrogen ($N_2$) or other sterile gas instead of air to provide the force recirculation, but it would disadvantageously result in very high costs of operation.

In prior art, and in particular in Ref. [AcienFernandez: 2003kh], it is described instead a small photobioreactor especially designed for production of blue-green algae loaded in $^{13}C$. It is of essence for this purpose that all the carbon provided for the growth of blue-green algae come from isotopically-labeled carbon. For this purpose, the plant is fed with a de-carbonated culture medium stored in a dedicated reservoir. Gas is bubbled through the small photobioreactor while being recirculated in a closed loop. The closed loop contains a feed line connecting to $^{13}CO_2$ reservoir, the source of isotopically-labeled carbon. The loop conveniently contains a processing unit for removal of DO, consisting of a simple 200 mL bubbling bottle with the gas bubbling in a sodium bisulphite solution. This arrangement allows to conveniently remove DO, but only if the concentration raises above the 110% saturation value. Inconveniently, the device is capable to efficiently strip DO completely from the culture medium. Also, inconveniently, the device does not include a culture medium recirculation system as in the devices equipped with an airlift system. It is therefore limited to small productions, of a few tens or hundreds of grams per year. It is unfit for larger production of many tens of hundreds of kg per year, as it will become of interest with the forthcoming increased availability of $^{13}C$ made possible as described in the patent application nr 102017000070755 filed by the same Applicant. It also lacks a temperature stabilization mechanism, and therefore it is not apt for field deployment and year-round operation.

OBJECTS AND SUMMARY OF THE INVENTION

It is an object of the present invention to overcome the drawbacks of the background art.

It is a further object of the present invention to describe a high-efficiency photobioreactor, able to produce tens to hundreds of kg per year of green/blue algae, that provides a volume for the cultivation of the blue-green algae that is easily and promptly put in complete separation from the atmosphere and leak-checked to guarantee the total absence of leaks to the atmosphere with the leak check standard of $<10^{-9}$ barxL/sec per single joint and $<10^{-8}$ mbarxL/sec for the entire photobioreactor, therefore suitable for the large scale production of green/blue algae labeled in $^{13}C$ with minimal if any dispersion of the valuable separated isotope in the environment.

It is a further object of the present invention to describe a high-efficiency photobioreactor, capable of operating with an efficient degasser able to strip all dissolved gases, including DO, a pollutant to the algae culture, to a reference, sub-atmospheric pressure level, thus reducing the concentration of DO to a small fraction of the atmospheric saturation value.

It is a further object of the present invention to describe a high-efficiency photobioreactor, where the continuous and rapid movement of the cultivation fluid required to prevent growth of algae on the surfaces of the photobioreactor is ensured by the presence of an innovative inert gas-push system, able to effectively accomplish the forced recirculation of the cultivation fluid while minimizing the shear and stress on the blue-green algae and being integrated with the vacuum degassing system.

It is a further object of the present invention to describe a high-efficiency photobioreactor, with the cultivation medium chamber constructed in glass or clear plastics or other clear material such as to maximally transmit the light responsible for the photosynthesis process.

It is a further object of the present invention to describe a high-efficiency photobioreactor, characterized by the presence of a thermal stabilization loop able to constantly maintain the temperature of the cultivation medium, year-round and throughout the 24 hours of the day-night cycle, within the narrow range mandated for the optimal growth of the specific blue-green algae in consideration, such as to maximize their production.

It is a further object of the present invention to describe a high-efficiency photobioreactor, possibly characterized by the presence of a illumination system providing light within the spectral range required for the optimal growth of the specific blue-green algae in consideration, such as to maximize their production.

It is a further object of the present invention to describe a high-efficiency photobioreactor, able to operate starting from a feed of liquid decarbonated or non-decarbonated culture medium that can be easily prepared to be stripped of any contamination coming from the atmosphere.

BRIEF DESCRIPTION OF THE INVENTION

This and further objects of the present invention will be advantageously realized by the construction of an innovative device for growth of blue-green algae, said device being a photobioreactor, comprising at least one vacuum-rated and solar receiver hosting the cultivation medium, comprising at least one vacuum-rated and solar receiver for the feed of decarbonated or non-decarbonate culture medium, comprising a gas loop, comprising the connection to a harvesting system for the collection of the final product, characterized by comprising an "inert gas-push" system comprising at least a circuit connection line, a circuit isolation valve, a gas shutoff valve, a downcomer, apt to open/interrupt the recirculation path of the cultivation medium by opening/closing said valves and such as to allow, alternatively and in a cyclical pattern, the flow of cultivation medium through valve or the rapid insertion in the vertical portion of the downcomer below the vertical circuit connection line and below valve of said system a volume of inert gas, the inert gas push system being thus able to force the recirculation of the cultivation medium while minimizing the stress and shear on the molecules of blue-green algae and avoiding introduction of dissolved oxygen.

In a preferred embodiment, the inert gas-push cultivation medium circulation system is combined with a vacuum degassing system consisting of a stripping column operating at sub-atmospheric pressure interfacing with the main circulation head, whose joint action at once provides the forced recirculation of the cultivation medium and the nearly complete removal of dissolved oxygen and other gases.

In a particularly preferred embodiment, said valve is selected for its large cross sectional opening and minimal dimension of the lip of the seat of its seal.

In a particularly advantageous embodiment, the circuit connection line and the downcomer will have diameters from 1 to 30 centimeters; preferably, valve will be a shutoff valve with the same diameter of the vertical circuit connection line and the downcomer, with the lip of the seat of its seal reduced to a dimension as minimal as possible, preferably below a few millimeters.

In a preferred embodiment said "inert gas push" is implemented by utilizing nitrogen gas as the inert gas, thus providing the advantage of using the inert gas most diffusely available for industrial use.

In a preferred embodiment said "inert gas push" is implemented by utilizing argon gas as the inert gas, thus providing the advantage of using the second inert gas most diffusely available for industrial use.

In a preferred embodiment said "inert gas push" is implemented by utilizing carbon dioxide gas or mixtures of nitrogen, argon and carbon dioxide as the inert gas, thus providing the advantage of directly providing as the push inert gas the feed necessary for the photosynthesis process of the blue-green algae.

In a preferred embodiment the photobioreactor with the "inert gas push" is complemented by a harvesting system containing a sift that permits to separate by filtration the blue-green algae and to save, after removal of the algae, the residual cultivation fluid, which can be destined for re-insertion in the solar receiver and in the head vessel system.

The combination of the inert gas-push system and of the degassing system is innovative and it permits to the construction and operation of the photobioreactor in a very advantageous manner: at once it reduces to a minimum the shear and stress on the molecules of the blue-green algae proliferating in the cultivation medium and reduces to a minimum, to the point of nearly complete removal, the concentration of dissolved oxygen, which imperils the growth of the blue-green algae.

This innovative device is achieved by introducing two important modifications to the traditional design of a "air lift" photobioreactor: first, rather than using air to lift the cultivation medium through the riser, the gas loop is used to push the cultivation medium down the downcomer by insertion of a volume of inert gas, thanks to the introduction of an on-off valve with a small seating area to minimize the shear and stress on the blue-green algae molecules; second, the volume of cultivation fluid displaced by the insertion of inert gas is at the same time displacing gas from the circulation head, a stripping column pumps away this gas being at sub-atmospheric base pressure from the circulation head through said stripping column, rising from bottom to top, and the cultivation medium being flown inside the circulation head through stripping column, falling from top to bottom, hence in countercurrent with respect to the gas flow, thus maximizing the surface-to-liquid exchange volume and permitting an efficient removal of the oxygen diffused in the cultivation fluid as a result of the photosynthetic process.

In particular, the present invention describes to a tubular photobioreactor for blue-green algae culture formed by a transparent, sealed tubular volume, coupled with a gas handling system designed to force the recirculation of the cultivation fluid through either an innovative inert gas-push system or a traditional air lift system, the gas handling system also being able, as said, to remove the oxygen produced by the growth of the blue-green algae and displace it with nitrogen or other inert gas, the gas handling system also being apt to save and recycle the trace carbon dioxide gas required for the blue-green algae growth the tube of the tubular system containing at its core a second opaque tube serving as a heat exchanger for the stabilization of temperature in the cultivation fluid.

This innovative device is designed to permit to recover the heat from low-temperature heat sources to stabilize the temperature of the cultivation fluid in a range optimal for the growth of the blue-green algae and to permit their optimal growth in a fluid in which the content of gaseous oxygen is required. This innovative device also permits to grow blue-green algae labeled with the stable isotope $^{13}C$ while eliminating or minimizing any loss of the $^{13}C$-labeled carbon dioxide, $^{13}CO_2$.

In a particular preferred embodiment, the innovative functioning of said photobioreactor can be reformulated and described also as an innovative method according to the above described photobioreactor, correlated to said photobioreactor, this being comprised in the content of the present invention

BRIEF DESCRIPTION OF THE DRAWINGS

This and more advantages obtained thanks to the here described innovative device for production of blue-green algae will be further described hereinafter with reference to non-limitative examples, which are provided for explanatory, non-limitative purposes in the accompanying drawings. These drawings illustrate different aspects and embodiments of this invention and, where appropriate, the structures, components, materials and/or similar elements are indicated in the different FIGURES with similar reference numbers.

FIG. 1 illustrates a preferred embodiment of the device for production of blue-green algae known as photobioreactor.

While the invention is susceptible to various modifications and alternative constructions, some of the illustrated embodiments are shown in the drawings and will be described below in detail.

It must be understood, however, that there is no intention to limit the invention to the specific illustrated embodiments, but, on the contrary, the invention intends to cover all the modifications, alternative constructions and equivalents that fall within the scope of the invention as defined in the claims.

The use of "such as", "etc.", "or" indicates non-exclusive alternatives without limitations, unless otherwise indicated.

The use of "includes" means "includes, but is not limited to", unless otherwise indicated.

FIG. 1 illustrates a preferred embodiment of the device 100 for production of blue-green algae known as photobioreactor.

DETAILED DESCRIPTION OF THE DRAWINGS

The photobioreactor 100 according to the embodiment described here below in particular comprises at least: one vacuum-rated solar receiver 800 hosting a cultivation medium shown as 1001 and filling completely said solar receiver 800, a head vessel system 700, located above the solar receiver, partially filled with the cultivation medium 1001 and partially filled with inert gas, a culture medium feed system 400 for the for the feed of decarbonated or non-decarbonate culture medium 1002, a carbon dioxide feed system 500, allowing the insertion of the carbon dioxide 1004, preferably labeled with the stable isotope $^{13}C$, which enables the photosynthesis of the blue-green algae, a harvesting system 600 for the collection of the cultivation medium 1002 matured as final product 1003 ready for processing for extraction of the blue-green algae, a gas loop 300, and characterized by the presence of an "inert gas-push" system 200, comprising a vertical circuit line 201 connecting the head vessel system 700 to a circuit isolation valve 202 which is in turn connect to a downcomer 203 connecting to the solar receiver 800, said system 200 also comprising a gas shutoff valve 204, said inert gas-push system 200 realized to open/interrupt the recirculation path of the cultivation medium 1001 by opening/closing said valves 202 and 204 such as to allow, alternatively and in a cyclical pattern, the flow of cultivation medium 1001 through valve 202 or the rapid insertion in the vertical portion of the downcomer 203 below the vertical circuit connection line 201 and below valve 202 of said system 200 a volume of inert gas, the inert gas push system being thus able to force the recirculation of the cultivation medium while minimizing the stress and shear on the molecules of blue-green algae and avoiding introduction of dissolved oxygen, having been said valve 202 selected for its large cross sectional opening and minimal dimension of the lip of the seat of its seal.

The solar receiver 800 contains most of the cultivation fluid and is made of transparent glass tubes 810, or clear plastic tubes, or other materials tubes, arranged to cover a very large surface. It is typically made of straight tubes and "U" tubes connected through joints that allow easily to assemble and disassemble the overall receiver to enable the initial installation as well as routine maintenance and/or cleaning procedures. It is provided by at least one couple of connection ports 801 through which an internal serpentine 802 is introduced, carrying a thermal exchange fluid to allow temperature stabilization within the range most proficient for the growth of the blue-green algae of interest.

The head vessel system 700 comprises a head vessel 710, equipped with its burst disk 701, its evacuation port connected to valve 702, and its product line 705, and its feed valve 703, connecting to the culture medium injection line 704, through which the culture medium 1002 is injected in the vessel head and from there in the solar receiver to become the cultivation medium 1001. The head vessel 710 connected to the solar receiver 800 through the riser 204 and the downcomer 203.

The herein described inert gas-push system differs from the traditional airlift system due to the presence of the main recirculation valve 202, a controlled on-off valve with high repetition rate, and of the gas injection line 304, connected to the downcomer through the gas injection valve 204.

Also differing from the traditional airlift system is the presence of the gas stripping column 720 integrated into the top portion of the head vessel. Comprised in the photobioreactor 100 and directly connected to the top of the stripping column 720 is the gas loop 300, comprising at least a gas extraction line 301, a vacuum/pump compressor 310, with its feedback line 311 and back-pressure regulating valve 312, a DO removal vessel 320, equipped with its burst disk 321, its evacuation port connected to valve 322, its stock feed valve 323, and its drain valve 324, and a buffer tank 19, connecting to the oxygen removal vessel 330 through the connection line 303, which is in turn connected to the downcomer through valve 204.

In a preferred embodiment, the oxygen removal vessel will contain a chemical fluid acting as an oxygen scavenger, such as sodium bisulphite or possibly other fluids, able to selectively remove oxygen by chemical reaction without removing the inert gas introduced to enable the forced recirculation of the cultivation medium and the carbon dioxide 1004 introduced to enable the photosynthesis of the blue-green algae.

In a preferred embodiment, the oxygen removal system/gas loop 300 shown in the drawing can be substituted by the combination of pressure-swing adsorption units and/or distillation columns.

The reactor 100 comprises also a culture medium feed system 400 comprising the culture medium tank 404, equipped with its burst disk 401, its evacuation port connected to valve 402, its stock feed valve 403, its inert gas purge injection valve 405, its drain valve 407, and the two connection lines 408 and 409, respectively connecting to the inert gas purge valve 405 and to the feeding pump 410. Shown is also the culture medium 1002. The culture medium feed system is activated during the commissioning of the system and whenever the cultivation fluid in the solar receiver 800 and in the head vessel 710 needs to be replenished. The evacuation port 402 allows to evacuate and leak check the culture medium vessel during the preparation phase; it also allows to evacuate the culture medium tank prior to start of the first loading with the culture medium, such as to minimize any residual contamination from atmospheric gases. During the first loading of the culture medium feed system, the fluid is loaded through the feed stock valve 403; then any residual contamination from atmospheric gases is again minimized by pumping an inert gas (nitrogen, argon, etc.) from valve 405 through connection line 408 into the vessel, where the inert gas is vigorously bubbled in the fluid, eventually escaping through the evacuation port 402, which for the purpose can be equipped with a system preventing gas reflux, such as an oil bubbler. The culture medium is loaded into the head vessel 710 and then into the solar receiver 810 through line 409, pump 410, line 704, and valve 703.

During regular operation, the cultivation medium contained in the head vessel 710 and in the solar receiver 800/810 is subject to continuous and forced recirculation. Specifically, the cultivation medium recirculates from the head vessel 710 through valve 202 through the downcomer 203 to the solar receiver 810, then into the riser 204 and to the stripping column 720, to return to the head vessel 710. This forces recirculation is achieved by an innovative system called inert gas-push system.

The inert gas-push system works by cyclically alternating on and off valve 202, thus forcing the system between alternate stationary and push phases, each lasting for only a few seconds.

During regular operation, during both the stationary and the push phases, pump 310 is in constant and continuous operation, and maintains the vessel circulation head 710 under partial vacuum, with a base pressure in the head vessel oscillating between a minimum and a maximum, around a goal value set feedback line 311 and back-pressure regulating valve 312.

During regular operation, during the stationary phase, after the precedent push phase and before the start of the following push phase, the valve 202 is open and the valve 204 is closed, and the cultivation fluid 1001 fills completely the downcomer 203 of the inert gas system 200. The cultivation fluid is stationary. The phase lasts for a few seconds, till the start of the following push phase.

During regular operation, at the beginning of a push phase, which takes place after the precedent stationary phase and before the following stationary phase, valve 203 is closed and immediately after valve 204 is open. Gas is injected in the from the gas injection line 304 to the downcomer 203, which displaces the cultivation fluid medium for a good portion of its vertical extension (but short of its full vertical extension, to prevent injection of gas in the solar receiver region). The cultivation medium being a fluid nearly incompressible, it is displaced in the downcomer 203 by the gas injected through valve 204, and as a consequence it pushes fluid up through the riser solar receiver 810 through the vertical riser 204 into the stripping column 720 and finally in the head vessel 710. The volume of cultivation medium displaced in one shot into the head vessel from the riser 204 is equal to the volume of gas displacing the cultivation fluid in the downcomer 203. As the single-shot volume of cultivation fluid mentioned and quantified above enters into the stripping column 720 and into the head vessel 710, due to the valve 202 being blocked, an equal volume of gas must be removed from the vessel head: this is accomplished by the pump 310, which pumps away gas from the vessel head 710 through the DO removal vessel 320 and eventually to the buffer tank 330.

One crucial feature of the inert gas-push system is that the gas pumped away from the circulation head 710 moves through the stripping column 720 in countercurrent with respect to the cultivation medium: gas rises at sub-atmospheric pressure through the column, from bottom to top, while the cultivation fluid falls through the column, from its injection point to the bottom. Due the countercurrent motion of cultivation medium and gas, the net action is that of providing the optimal gas stripping of the cultivation fluid in a regime of partial vacuum, at a value of the pressure cyclically oscillating around the pressure set by the feedback line 311 and back-pressure regulating valve 312.

As described above for the case of the culture medium feed system, the evacuation valves 702, 322, and 402 can be used during the initial preparation for commissioning of the photobioreactor to evacuate it completely, which is necessary to perform a detailed leak check as well as to remove any atmospheric contamination. The batch of inert gas required to prime the system can be inserted through valves 405 in the culture medium tank, and from there in the head vessel 710 and in the solar receiver 810 through isolation valve 406, line 409, pump 410, line 704, and isolation valve 703. The inert gas can also be used, with valve 405 open, isolation valve 406 closed, and valve 402 open and with a no return gas system (such as an oil bubbler) connected to it, to purge the culture medium 1002 before this is pumped from the culture medium vessel 404 into the circulation head 710 through isolation valve 406, line 409, pump 410, line 704, and isolation valve 703.

The harvesting system 600 comprises the harvesting vessel 610, connected to the main circulation head 710 through line 705 and valve 603, equipped with its burst disk 601, its evacuation port connected to valve 602, and its drain valve 604.

Also crucial is the present of the carbon dioxide insertion system 500, designed to load the cultivation medium with either regular of $^{13}C$-labeled carbon dioxide 1004, comprising pressure vessel 503, valve 501 connecting to the solar receiver 810/800, and valve 502, which can at once serve for the initial evacuation and leak checking as well as a feeding valve.

Please note that to the present innovative photobioreactor system it can be related also a method to perform the described operations: as the method is intrinsically part of the functioning of the system, Applicant hereby does not describe a method as separated content, but it would also be possible to describe an operating method related to the photobioreactor system, which would certainly fall within the scope of the present invention and would be protected by the description of the present invention. So it would be possible to insert the description of a method for the operation of the photobioreactor system herein described without adding any subject matter to the present invention, but only describing further embodiments to eventually better clarify the scope of the present invention.

So it appears clear how the present invention permits so solve all the hereinabove cited technical problems thanks to the innovative photobioreactor system 100 described by the present invention, with particular reference of the here described preferred embodiment, please note that any change in the order of the components, o in non substantially details of the operations, number of the valves, number/type of the tubes, kind of gas used, amount of production, dimension of the plant, operative temperatures, number of operation cycles, dimension of the single constitutive elements, materials used for the realization of the system, are to be considered only non-significant modifications of some realizations embodiment of the present invention and have to be considered covered by the object of the present invention as here above described and better explicated with reference to the annexed claims.

BIBLIOGRAPHY

[Shih:2009gb] C.-M. Shih, S.-N. Cheng, C.-S. Wong, Y.-L. Kuo, and T.-C. Chou, Anesthesia & Analgesia 108, 1303 (2009).

[Farooq:2014hy] S. M. Farooq, N. B. Boppana, D. Asokan, S. D. Sekaran, E. M. Shankar, C. Li, K. Gopal, S. A. Bakar, H. S. Karthik, and A. S. Ebrahim, PLoS ONE 9, e93056 (2014).

[Kamarei:1985gk] A. R. Kamarei, Z. Nakhost, and M. Karel, SAE Technical Paper 851388, (1985).

[Parikh:2001fs] P. Parikh, U. Mani, and U. Iyer, Journal of Medicinal Food 4, 193 (2001).

[Mazokopakis:2013bu] E. E. Mazokopakis, I. K. Starakis, M. G. Papadomanolaki, N. G. Mavroeidi, and E. S. Ganotakis, Journal of the Science of Food and Agriculture 94, 432 (2013).

[TorresDuran:2007ba] P. V. Torres-Duran, A. Ferreira-Hermosillo, and M. A. Juarez-Oropeza, Lipids in Health and Disease 6, 33 (2007).

[Park:2008ks] H. J. Park, Y. J. Lee, H. K. Ryu, M. H. Kim, H. W. Chung, and W. Y. Kim, Annals of Nutrition and Metabolism 52, 322 (2008).

[Ismail:2015hf] M. Ismail, M. F. Hossain, A. R. Tanu, and H. U. Shekhar, BioMed Research International 2015, 1 (2015).

[Ku:2013ck] C. S. Ku, Y. Yang, Y. Park, and J. Lee, Journal of Medicinal Food 16, 103 (2013).

[Lee:2008fy] E. H. Lee, J.-E. Park, Y.-J. Choi, K.-B. Huh, and W. Y. Kim, Nutrition Research and Practice 2, 295 (2008).

[Ismail:2009up] M. F. Ismail, D. A. Ali, A. Fernando, M. E. Abdraboh, R. L. Gaur, W. M. Ibrahim, M. H. G. Raj, and A. Ouhtit, International Journal of Biological Sciences 5, 377 (2009).

[Akao:2009hp] Y. Akao, T. Ebihara, H. Masuda, Y. Saeki, T. Akazawa, K. Hazeki, O. Hazeki, M. Matsumoto, and T. Seya, Cancer Science 100, 1494 (2009).

[Mathew:1995fj] B. Mathew, R. Sankaranarayanan, P. P. Nair, C. Varghese, T. Somanathan, B. P. Amma, N. S. Amma, and M. K. Nair, Nutrition and Cancer 24, 197 (1995).

[Bhavana:2013hp] S. M. Bhavana, Journal of Clinical and Diagnostic Research 7, 3048 (2013).

[Selmi:2011im] C. Selmi, P. S. Leung, L. Fischer, B. German, C.-Y. Yang, T. P. Kenny, G. R. Cysewski, and M. E. Gershwin, Cellular & Molecular Immunology 8, 248 (2011).

[Kalafati:2010ho] M. Kalafati, A. Z. Jamurtas, M. G. Nikolaidis, V. Paschalis,
A. A. Theodorou, G. K. Sakellarious, Y. Koutedakis, and D. Kouretas, Medicine & Science in Sports & Exercise 42, 142 (2010).

[Lu:2006je] H.-K. Lu, C.-C. Hsieh, J.-J. Hsu, Y.-K. Yang, and H.-N. Chou, European Journal of Applied Physiology 98, 220 (2006).

[Ou:2012jw] Y. Ou, L. Lin, Q. Pan, X. Yang, and X. Cheng, Environmental Toxicology and Pharmacology 34, 721 (2012).

[Ou:2013gf] Y. Ou, L. Lin, X. Yang, Q. Pan, and X. Cheng, Pharmaceutical Biology 51, 539 (2013).

[Jarouliya:2012uy] U. Jarouliya, J. A. Zacharia, P. Kumar, P. S. Bisen, and G. B. K. S. Prasad, The Indian Journal of Medical Research 135, 422 (2012).

[AcienFernandez:2001en] F. G. Aden Fernandez, J. M. Fernandez Sevilla, J. A. Sánchez Pérez, E. Molina Grima, and Y. Chisti, Chemical Engineering Science 56, 2721 (2001).

[AcienFernandez:2003kh] F. G. Adén Fernández, C. B. Alias, J. A. Sánchez Pérez, J. M. Fernández Sevilla, M. J. Ibáñez González, and E. M. Grima, Journal of Applied Phycology 15, 229 (2003).

The invention claimed is:

1. A device (100) for growth of blue-green algae, said device being a photobioreactor (100), comprising at least one vacuum-rated and solar receiver (800) hosting a cultivation medium (1001), and filling completely said solar receiver (800) with the cultivation medium (1001), a head vessel system (700), located above the solar receiver, partially filled with the cultivation medium (1001) and partially filled with inert gas, a culture medium feed system (400) for the feed of decarbonated or non-decarbonated culture medium (1002), a carbon dioxide feed system (500), allowing the insertion of the carbon dioxide (1004), which enables the photosynthesis of the blue-green algae, a harvesting system (600) for the collection of the decarbonated or non-decarbonated culture medium (1002) matured as final product (1003) ready for processing for extraction of the blue-green algae, a gas loop (300), wherein the device comprising an "inert gas-push" system (200) comprising at least a circuit connection line (201), a circuit isolation valve (202), a gas shutoff valve (204), a downcomer (203), apt to open/interrupt the recirculation path of the cultivation medium (1001) by opening/closing said valves (202,204) and such as to allow, alternatively and in a cyclical pattern, the flow of cultivation medium (1001) through the circuit isolation valve (202) or the rapid insertion in the vertical portion of the downcomer (203) below the vertical circuit connection line (201) and below the circuit isolation valve (202) of said system (200) a volume of inert gas, wherein the "inert gas-push" system (200) is combined with the head vessel system (700) consisting of a stripping column (720) operating at sub-atmospheric pressure interfacing with a main circulation head (710), whose joint action at once provides the forced recirculation of the cultivation medium and the nearly complete removal of dissolved oxygen, the "inert gas-push" system (200) being thus able to force the recirculation of the cultivation medium while minimizing the stress and shear on the molecules of blue-green algae and avoiding introduction of dissolved oxygen.

2. The device for growth of blue-green algae according to claim 1, wherein said circuit isolation valve (202) has a specific cross sectional opening and a specific dimension of the lip of a seat of a seal of the circuit isolation valve (202).

3. The device for growth of blue-green algae according to claim 1, wherein the circuit connection line (201) and the downcomer (203) have diameters from 1 to 30 centimeters; the gas shut off valve (204) will be a shutoff valve with the same diameter of the vertical circuit connection line and the downcomer (203), with a lip of a seat of a seal of the circuit isolation valve (202) reduced to a specific dimension.

4. The device (100) for growth of blue-green algae according to claim 1, said "inert gas-push" system (200) is implemented by utilizing nitrogen gas as the inert gas or by utilizing argon gas as the inert gas or is implemented by utilizing carbon dioxide gas or mixtures of nitrogen, argon and carbon dioxide as the inert gas, directly providing the push inert gas the feed necessary for the photosynthesis process of the blue-green algae.

5. The device (100) for growth of blue-green algae according to claim 1, wherein the photobioreactor with the "inert gas-push" system (200) is complemented by a harvesting system containing a sift that permits to separate by filtration the blue-green algae and to save, after removal of the algae, the residual cultivation medium, which can be destined for re-insertion in the solar receiver and in the head vessel system.

6. The device (100) for growth of blue-green algae according to claim 1, wherein the combination of the "inert gas-push" system (200) and of a degassing system permits the construction and operation of the photobioreactor reducing to a minimum the shear and stress on the molecules of the blue-green algae proliferating in the cultivation medium and reducing to a minimum, to the point of nearly complete removal, the concentration of dissolved oxygen, which imperils the growth of the blue-green algae.

7. The device for growth of blue-green algae according to claim 1, wherein an "air lift" photobioreactor of said device uses the gas loop (300) to push the cultivation medium down the downcomer by insertion of a volume of inert gas, comprising an on-off valve with a specific seating area to minimize the shear and stress on the blue-green algae molecules, and more the volume of cultivation medium displaced by the insertion of inert gas is at the same time displacing gas from the main circulation head, a stripping column pumps away this gas being at sub-atmospheric base pressure from the main circulation head through said stripping column, rising from bottom to top, and the cultivation medium being flown inside the main circulation head through the stripping column, falling from top to bottom, hence in countercurrent with respect to the gas flow, thus maximizing the surface-to-liquid exchange volume and permitting an efficient removal of the oxygen diffused in the cultivation medium as a result of the photosynthetic process.

8. The device (100) for growth of blue-green algae according to claim 1, wherein the photobioreactor is a tubular photobioreactor for blue-green algae culture formed by a transparent, sealed tubular (810) volume, coupled with a gas handling system designed to force the recirculation of the cultivation medium through either the "inert gas-push" system or a traditional air lift system, the gas handling system also being able to remove the oxygen produced by the growth of the blue-green algae and displace it with nitrogen or other inert gas, the gas handling system also being apt to save and recycle the trace carbon dioxide gas required for the blue-green algae growth, the tube of the tubular system containing at its core a second opaque tube serving as a heat exchanger for the stabilization of temperature in the cultivation medium.

9. The device (100) for growth of blue-green algae according to claim 1, wherein said device permits to recover the heat from specific-temperature heat sources to stabilize the temperature of the cultivation medium in a range optimal for the growth of the blue-green algae and to permit their optimal growth in a fluid in which the content of gaseous oxygen is required, and the device permits to grow blue-green algae labeled with the stable isotope (13C) while eliminating or minimizing any loss of the 13C-labeled carbon dioxide, (13CO2).

* * * * *